United States Statutory Invention Registration [19]

[11] Reg. Number: H243

Sapienza et al. [43] Published: Apr. 7, 1987

[54] CATALYSTS FOR THE PRODUCTION OF HYDROCARBONS FROM CARBON MONOXIDE AND WATER

[75] Inventors: Richard S. Sapienza, Shoreham; William A. Slegeir, Hampton Bays; Robert I. Goldberg, Selden, all of N.Y.

[73] Assignee: The United States of America as represented by the United States Department of Energy, Washington, D.C.

[21] Appl. No.: 797,509

[22] Filed: Nov. 6, 1985 (Under 37 CFR 1.47)

[51] Int. Cl.[4] ..... C07C 27/08

[52] U.S. Cl. ..... 518/701; 518/700; 518/711

*Primary Examiner*—John F. Terapane
*Assistant Examiner*—Jack Thomas
*Attorney, Agent, or Firm*—Hugh W. Glenn; Robert J. Fisher; Judson R. Hightower

[57] ABSTRACT

A method of converting low $H_2/CO$ ratio syngas to carbonaceous products comprising reacting the syngas with water or steam at 200° to 350° C. in the presence of a metal catalyst supported on zinc oxide. Hydrocarbons are produced with a catalyst selected from cobalt, nickel or ruthenium and alcohols are produced with a catalyst selected from palladium, platinium, ruthenium or copper on the zinc oxide support. The ratio of the reactants are such that for alcohols and saturated hydrocarbons:

$$(2n+1) \geqq x \geqq 0$$

and for olefinic hydrocarbons:

$$2n \geqq x \geqq 0$$

where n is the number of carbon atoms in the product and x is the molar amount of water in the reaction mixture.

5 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

CATALYSTS FOR THE PRODUCTION OF HYDROCARBONS FROM CARBON MONOXIDE AND WATER

CONTRACTUAL ORIGIN OF THE INVENTION

The United States Government has rights in this invention pursuant to Contract No. DE-AC0-2-76CH00016 between the U.S. Department of Energy and Associated Universities, Inc.

BACKGROUND OF THE INVENTION

Syngas, a mixture of carbon monoxide and hydrogen, is widely employed in the catalytic production of hydrocarbons, alcohols and mixtures of these products.

Typically for the production of saturated hydrocarbons and olefins the reaction is carried out in a reaction inert liquid medium containing suspended catalyst. Typical catalysts include iron and cobalt normally absorbed on a carrier such as thorium, magnesium oxide or kieselguhr. To produce alcohols, noble metals on the same supports are often used.

The usual source of syngas is the gasification reaction in which water vapor is reacted with a source of carbon, usually coal, under known conditions. The reaction is endothermic and a common source of heat for the reaction is to burn some of the coal by reaction with oxygen. The theoretical reaction including the burning is:

$$2C + H_2O + \tfrac{1}{2}O_2 \rightarrow 2CO + H_2$$

so that the theoretical ratio of carbon monoxide to hydrogen in the reaction product is 2:1.

For the production of methane, the theoretical reaction is:

$$CO + 3H_2 \rightarrow H\text{-}(CH_2)\text{-}H + H_2O$$

and the general reaction for the production of higher saturated hydrocarbons is:

$$nCO + (2n+1)H_2 \rightarrow (CH_2H)_nH + nH_2O$$

It is thus apparent that the ideal ratio of hydrogen to carbon monoxide in feed gas for the production of saturated hydrocarbons is between 2:1 and 3:1. The theoretical ratio in syngas, as shown above is only 1:2. In fact the "real world" actual ratio in the usual industrial operation is about 0.5:1 to 0.8:1 in syngas.

To compensate for the missing hydrogen, the usual commercial practice is to mix the syngas with water vapor as an additional hydrogen source.

The theoretical reaction which takes place in this case is represented by the equation:

$$(n + x)\,CO + (2n + 1 - x)\,H_2 + xH_2O \;\downarrow\; H(CH_2)_nH + nH_2O + xCO_2$$

where n is the number of carbon atoms in the saturated hydrocarbon produced, and x is the number of moles of water.

To conduct this reaction at maximum efficiency using the low ratio syngas industrially available, iron and cobalt are the most widely employed catalysts. Iron is advantageous because it is "flexible" which means that it will accept and operate reasonably efficiently with low ratio syngas in which the ratio of hydrogen to carbon monoxide varies over a wide range. However, iron requires the use of high temperatures and the rate of reaction is relatively low. The use of cobalt gives rise to higher reaction rates, but cobalt is not flexible and is sensitive to temperatures above 250° C.

The generalized equation for the production of olefinic hydrocarbons is:

$$(n + x)CO + \left(\frac{3n}{2} - x + 1\right) H_2 + xH_2O \;\downarrow\; H(CH{=}CH)_{n/2}H + nH_2O + xCO_2$$

The problems experienced with this reaction are similar to the problems experienced for the production of saturated hydrocarbons.

When a syngas-water mixture is employed to produce alkanols, the theoretical equation is:

$$(n + x)\,CO + (2n - x)\,H_2 + xH_2O \;\downarrow\; H(CH_2)_nOH + (n - 1)\,H_2O + xCO_2$$

The catalysts normally employed in the reaction have been palladium, platinum, iridium, copper and ruthenium with or without a carrier. These catalysts have proved to be flexible like iron, but they also suffer the same disadvantages as iron. They require high temperatures, and the rate of reaction is low.

DESCRIPTION OF THE INVENTION

It has now been discovered that the reactions discussed above can be conducted with low ratio syngas, at low temperature, at good rates to give high yields of the desired products by the use of selected catalysts under defined conditions. The process of the invention is also very flexible, that is it is able to accommodate itself to a wide range of hydrogen to carbon monoxide ratios.

More specifically, it has been discovered that saturated hydrocarbons can be produced in good yield if the reaction between carbon monoxide, hydrogen and water is suspended preferably at a temperature of from 225° to 275° C. under conditions such that the relative concentration of the reactants is expressed by the formula:

$$(2n+1) \geqq x \geqq 0$$

where n and x have the same meaning as above.

For the production of olefinic hydrocarbons the operative monounsaturated formula is:

$$2n \geqq x \geqq 0$$

For the production of alkanols the operative formula is the same as for the production of saturated hydrocarbons.

The temperature range for the production of olefins and alkanols is the same as for the production of saturated hydrocarbons.

The catalysts employed on this invention are all supported on zinc oxide. For the production of saturated hydrocarbons and olefins, the catalysts are cobalt, nickel, ruthenium, or mixtures thereof supported on zinc oxide. For the production of alkanols, the catalysts on the zinc oxide support are palladium, platinum, iridium, copper, rhodium, or mixtures thereof.

The supported catalysts are prepared by the deposition of the catalytic metal on zinc oxide. Typically, this is accompanied by impregnation of the support with an aqueous solution of a salt of the particular metal. Such preparations are shown, for example, in U.S. Pat. No. 3,988,334, incorporated herein by reference. In the usual process, as applied to the preparation of a supported catalyst of this invention, zinc oxide in particulate form is immersed in an aqueous solution of a salt of the selected metal. After sufficient time for impregnation of the support, the mixture is dried at temperatures between 80° C. and 200° C., usually in air, and ultimately calcined in air for a period of from about one half to one and one half hour temperatures from 300° C. to 600° C. Other techniques, well known to those skilled in the art include sputtering, and other methods of deposition including vapor deposition, electrical deposition and electrochemical deposition.

The process of this invention is conducted in a slurry using conventional equipment. The selected catalyst is taken up in the liquid medium to form a suspension of the catalyst at a concentration of from about 10 to 60 percent by volume. Concentrations of from about 25 to 50 g/l are preferred.

Suitable temperature range for conducting the process of the present invention is from about 200° C. to 350° C., preferably from 225° C. to 275° C.

The pressures at which the reaction is carried out can vary over a wide range provided they are selected so that the parameters defined by the above formulas are observed. Typically, and preferred partial pressures for hydrogen, carbon monoxide and steam are as follows:

| | Typical psi | Preferred psi |
|---|---|---|
| Hydrogen | 1500 to 0 | 750 to 25 |
| Carbon monoxide | 1500 to 15 | 1000 to 100 |
| Steam | 500 to 1 | 300 to 25 |

Control of the partical pressures of the reactants is used to control the number of moles of the reactants, thereby assuring that the above defined parameters are observed.

Typically, the reactants are charged into an autoclave containing a suspension of the selected supported catalyst. The autoclave is sealed and brought to the reaction temperature. The pressure increases to the desired range and then starts to decrease indicating that reaction is taking place.

Those skilled in the art will recognize that reactions of this type produce mixtures of products. Thus, for example, in the production of hydrocarbons the reaction can be conducted within the parameters above defined to produce principally ethane, but the reaction mixture will contain small amounts of other hydrocarbons such as methane, propane and butane.

The following non-limiting examples are given by way of illustration,

EXAMPLE 1

Platinum is deposited on 10 g zinc oxide by impregnation. This catalyst is slurried in a solvent system of 100 ml consisting of 1 part tetrahydrofuran and 5 parts cyclohexane. This is introduced into a 500 ml stirred pressure reactor with 12 ml of water. The reactor is pressurized with 500 psi carbon monoxide and 500 psi hydrogen, heated to 240° C. and stirred at 750 rpm. After 5 hours, pressure is released and products analyzed by gas chromatography. Methanol is the sole product.

EXAMPLE 2

Cobalt is substituted for platinum in Example 1. Hydrocarbon products including methane, ethane, propane and higher products are found.

EXAMPLE 3

Cobalt and copper are deposited from basic solutions onto zinc oxide support for use as the catalyst. The products from a process similar to that of Example 1, include mixed alcohols and hydrocarbons.

Although the present invention is described in terms of specific materials and process steps, it will be clear to one skilled in the art that various modifications may be made consistent with the scope of the accompanying claims.

The embodiments of this invention in which an exclusive property of privilege is claimed are defined as follows:

1. A method for the reaction of a mixture of carbon monoxide, hydrogen and water for the production of at least one carbonaceous product selected from the group consisting of hydrocarbons, alcohols and mixture thereof comprising contacting the reactants together in a slurry containing a catalyst suspended in a reaction inert liquid medium at a temperature of from about 200° to 350° C., the catalyst being on a zinc oxide support and being selected from the group consisting of cobalt, nickel, ruthenium, palladium, platinum, iridium, rhodium, copper and mixtures thereof.

2. The method of claim 1, for the production of hydrocarbons wherein the inert liquid medium with catalyst is at a temperature of 225° C. to 275° C., the catalyst on a zinc oxide support is selected from the group consisting of cobalt, nickel, ruthenium and mixtures thereof.

3. The method of claim 2 for the production of saturated hydrocarbons wherein the ratio of reactants being such that:

$$(2n+1) \geqq x \geqq 0$$

where n being the number of carbon atoms in the product and x being the number of moles of water in the reaction mixture.

4. The method of claim 2 for the production of olefinic hydrocarbons wherein the ratio of reactants is such that:

$$2n \geqq x \geqq 0$$

where n is being the number of carbon atoms in the product and x being the number of moles of water in the reaction mixture.

5. The method of claim 1 for the production of alkanols wherein the inert liquid medium with catalyst is at a temperature of 225° C. to 275° C., the catalyst on zinc oxide support being selected from the group consisting of palladium, platinum, iridium, rhodium, copper and mixtures thereof and wherein the ratio of reactants is such that:

$$2n+1 \geqq x \geqq 0$$

where n being the number of carbon atoms in the product and x being the number of moles of water in the reaction mixture.

* * * * *